US008290303B2

(12) United States Patent
Washburn et al.

(10) Patent No.: US 8,290,303 B2
(45) Date of Patent: Oct. 16, 2012

(54) ENHANCED SYSTEM AND METHOD FOR VOLUME BASED REGISTRATION

(75) Inventors: Michael Joseph Washburn, Brookfield, WI (US); Markus Wilhelm Marquart, Eching (DE)

(73) Assignee: General Electric Company, Schenectady, NY (US)

( * ) Notice: Subject to any disclaimer, the term of this patent is extended or adjusted under 35 U.S.C. 154(b) by 1082 days.

(21) Appl. No.: 11/870,522

(22) Filed: Oct. 11, 2007

(65) Prior Publication Data

US 2009/0097778 A1    Apr. 16, 2009

(51) Int. Cl.
*G06K 9/36* (2006.01)
(52) U.S. Cl. ........ 382/294; 382/128; 382/132; 382/154; 128/922
(58) Field of Classification Search .......... 382/128, 382/131, 132, 154, 219, 278; 128/922
See application file for complete search history.

(56) References Cited

U.S. PATENT DOCUMENTS

| | | | |
|---|---|---|---|
| 5,353,354 A | 10/1994 | Keller et al. | |
| 5,608,849 A | 3/1997 | King, Jr. | |
| 5,672,877 A | 9/1997 | Liebig et al. | |
| 5,765,561 A | 6/1998 | Chen et al. | |
| 6,186,006 B1* | 2/2001 | Schmitz et al. | 73/598 |
| 6,266,453 B1 | 7/2001 | Hibbard et al. | |
| 6,490,476 B1* | 12/2002 | Townsend et al. | 600/427 |
| 6,500,123 B1 | 12/2002 | Holloway et al. | |
| 6,631,284 B2* | 10/2003 | Nutt et al. | 600/427 |
| 6,775,404 B1 | 8/2004 | Pagoulatos et al. | |
| 6,850,252 B1* | 2/2005 | Hoffberg | 715/716 |

(Continued)

FOREIGN PATENT DOCUMENTS

CN    1408102 (A)    4/2003

(Continued)

OTHER PUBLICATIONS

Pagoulatos et al.: "Interactive 3-D Registration of Ultrasound and Magnetic Resonance Images Based on a Magnetic Position Sensor", published in IEEE Transactions on Information Technology in Biomedicine, vol. 3, No. 4, Dec. 1999.

(Continued)

*Primary Examiner* — Yosef Kassa
(74) *Attorney, Agent, or Firm* — The Small Patent Law Group; Dean D. Small

(57) ABSTRACT

A method for volume based registration of images is presented. The method includes receiving a first image data set and at least one other image data set. Further the method includes identifying a first image slice in the at least one other image data set corresponding to the first image data set. The method also includes selecting a first point of interest on at least one of the first image data set or the first image slice in the at least one other image data set. In addition, the method includes selecting a second point of interest on the other of the first image data set or the first image slice in the at least one other image data set, wherein the second point of interest corresponds to the first point of interest. Moreover, the method includes translating one of the first image data set, the first image slice, or both, in a first direction, a second direction and a third direction to align the first point of interest with the second point of interest. Also, the method includes registering the first image data set and the at least one other image data set. Systems and computer-readable medium that afford functionality of the type defined by this method is also contemplated in conjunction with the present technique.

31 Claims, 8 Drawing Sheets

U.S. PATENT DOCUMENTS

| | | | |
|---|---|---|---|
| 7,020,313 B2 | 3/2006 | Declerck et al. | |
| 7,052,461 B2 | 5/2006 | Willis | |
| 7,295,706 B2 * | 11/2007 | Wentland et al. | 382/181 |
| 7,490,014 B1 * | 2/2009 | Koren et al. | 702/94 |
| 7,499,250 B2 * | 3/2009 | Zhang | 361/42 |
| 7,510,536 B2 * | 3/2009 | Foley et al. | 601/2 |
| 7,536,595 B1 * | 5/2009 | Hiltunen et al. | 714/26 |
| 7,578,079 B2 * | 8/2009 | Furem | 37/348 |
| 7,603,165 B2 * | 10/2009 | Townsend et al. | 600/427 |
| 7,613,501 B2 * | 11/2009 | Scherch | 600/427 |
| 7,620,229 B2 * | 11/2009 | Oosawa | 382/130 |
| 7,680,314 B2 * | 3/2010 | Hong | 382/131 |
| 7,717,849 B2 * | 5/2010 | Mathew et al. | 600/437 |
| 7,722,539 B2 * | 5/2010 | Carter et al. | 600/439 |
| 2004/0236206 A1 | 11/2004 | Sakas et al. | |
| 2006/0072808 A1 | 4/2006 | Grimm et al. | |

FOREIGN PATENT DOCUMENTS

| | | |
|---|---|---|
| CN | 1628325 (A) | 6/2005 |
| CN | 1639739 (A) | 7/2005 |
| CN | 1760915 (A) | 4/2006 |
| CN | 1973297 (A) | 5/2007 |
| CN | 101006465 (A) | 7/2007 |
| WO | WO 96/25881 | 8/1996 |

OTHER PUBLICATIONS

Hata, et al., Development of a Frameless and Armless Stereotactic Neuronavigation System With Ultrasonographic Registration, Neurosurgery, vol. 41, No. 3, Sep. 1997, (7) pgs.

N. Pagoulatos, et al., Calibration and Validation of Free-Hand 3D Ultrasound Systems Based on DC Magnetic Tracking, Part of the SPIE Conference on Image Display, San Diego, CA, Feb. 1998, SPIE vol. 3335, (13) pgs.

Cameron Ritchie, et al., Three-Dimensional Ultrasonic Angiography Using Power-Mode Doppler, Ultrasound in Med. & Biol., vol. 22, No. 3, pp. 277-286, 1996.

* cited by examiner

ENHANCED SYSTEM AND METHOD FOR VOLUME BASED REGISTRATION

BACKGROUND

The invention relates generally to imaging of an object, and more specifically to volume based registration of two or more images.

Image registration finds wide application in medical imaging, video motion analysis, remote sensing, security and surveillance applications. Further, the process of finding the correspondence between the contents of the images is generally referred to as image registration. In other words, image registration includes finding a geometric transform that non-ambiguously links locations and orientations of the same objects or parts thereof in the different images. More particularly, image registration includes transforming the different sets of image data to a common coordinate space. The images may be obtained by different imaging devices or alternatively by the same imaging device but at different imaging sessions or time frames. As will be appreciated, in the field of medical imaging, there has been a steady increase in the number of imaging sessions or scans a patient undergoes. Images of a body part may be obtained temporally from the same imaging modality or system. Alternatively, in multi-modal imaging, images of the same body parts may be captured via use of different imaging modalities such as an X-ray imaging system, a magnetic resonance (MR) imaging system, a computed tomography (CT) imaging system, an ultrasound imaging system or a positron emission tomography (PET) imaging system.

In medical registration, registration of images is confronted by the challenges associated with patient movement. For example, due to either conscious or unconscious movement of the patient between two scans obtained either via the same imaging modality or otherwise, there exists an unpredictable change between the two scans. Unfortunately, this change in position leads to misalignment of the images. Additionally, patient position may vary depending on the imaging modalities used for multi-modal scanning. For example, a patient may be positioned in the prone position (i.e., lying face down) for a magnetic resonance imaging (MRI) scanning session of the colon and may be in the supine position (i.e., lying face up) during the same type of exam using a different piece of imaging equipment such as an ultrasound machine. The differences in position create inherent registration problems.

Volume-guided ultrasound is an application in which an ultrasound image is registered with a previously acquired (pre-acquired) image volume. The pre-acquired volume data set may include a CT image data set, an MR image data set, a PET image data set, or an ultrasound image data set, for example. Previously conceived solutions to effect the registration of the ultrasound image with the pre-acquired volume data set include use of a position sensing system having one or more sensors mounted on or in the ultrasound transducer. However, the process of registering the ultrasound image to the pre-acquired volume data set may be laborious and time-consuming.

There is therefore a need for a design of a method and system capable of efficiently registering an ultrasound image with a pre-acquired image volume data set obtained via a single modality or a plurality of imaging modalities. In particular, there is a significant need for a design of a method and a system for registering images that enhances workflow efficiency while minimizing errors.

BRIEF DESCRIPTION

In accordance with aspects of the present technique, a method for volume based registration of images is presented. The method includes receiving a first image data set and at least one other image data set. Further the method includes identifying a first image slice in the at least one other image data set corresponding to the first image data set. The method also includes selecting a first point of interest in at least one of the first image data set or the first image slice in the at least one other image data set. In addition, the method includes selecting a second point of interest in the other of the first image data set or the first image slice in the at least one other image data set, where the second point of interest corresponds to the first point of interest. Moreover, the method includes translating one of the first image data set, the first image slice, or both, in a first direction, a second direction and a third direction to align the first point of interest with the second point of interest. Also, the method includes updating registration of the first image data set and the at least one other image data set. Computer-readable medium that afford functionality of the type defined by this method is also contemplated in conjunction with the present technique.

In accordance with yet another aspect of the present technique, a method for volume based registration of images is presented. The method includes receiving a first image data set and at least one other image data set. Additionally, the method includes identifying a location in the first image data set, where the location is in a known orientation to one or more image slices in the at least one other image data set. Also, the method includes selecting a first point of interest in at least one of the first image data set or the at least one other image data set. Furthermore, the method includes selecting a second point of interest in the other of the first image data set or the at least one other image data set, where the second point of interest corresponds to the first point of interest. In addition, the method includes translating one of the first image data set, the at least one other image data set, or both, in a first direction, a second direction and a third direction to align the first point of interest with the second point of interest. The method also includes updating registration of the first image data set and the at least one other image data set.

In accordance with further aspects of the present technique, a system is presented. The system includes at least one imaging system configured to obtain a first image data set and at least one other image data set. In addition, the system includes a processing sub-system operationally coupled to the at least one imaging system and configured to process each of the first image data set and the at least one other image data set to generate a registered image based upon a volume based registration of the first image data set and the at least one other image data set.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As will be described in detail hereinafter, an imaging system capable of volume based registration of images, and methods of volume based registration are presented. Workflow efficiency may be enhanced while minimizing errors by employing the system and methods of volume based registration of images. Although, the exemplary embodiments illustrated hereinafter are described in the context of a medical imaging system, it will be appreciated that use of the imaging system capable of volume based registration of images in industrial applications are also contemplated in conjunction with the present technique. The industrial applications may include applications, such as, but not limited to, baggage scanning applications, and other security and surveillance applications.

Figure 1:
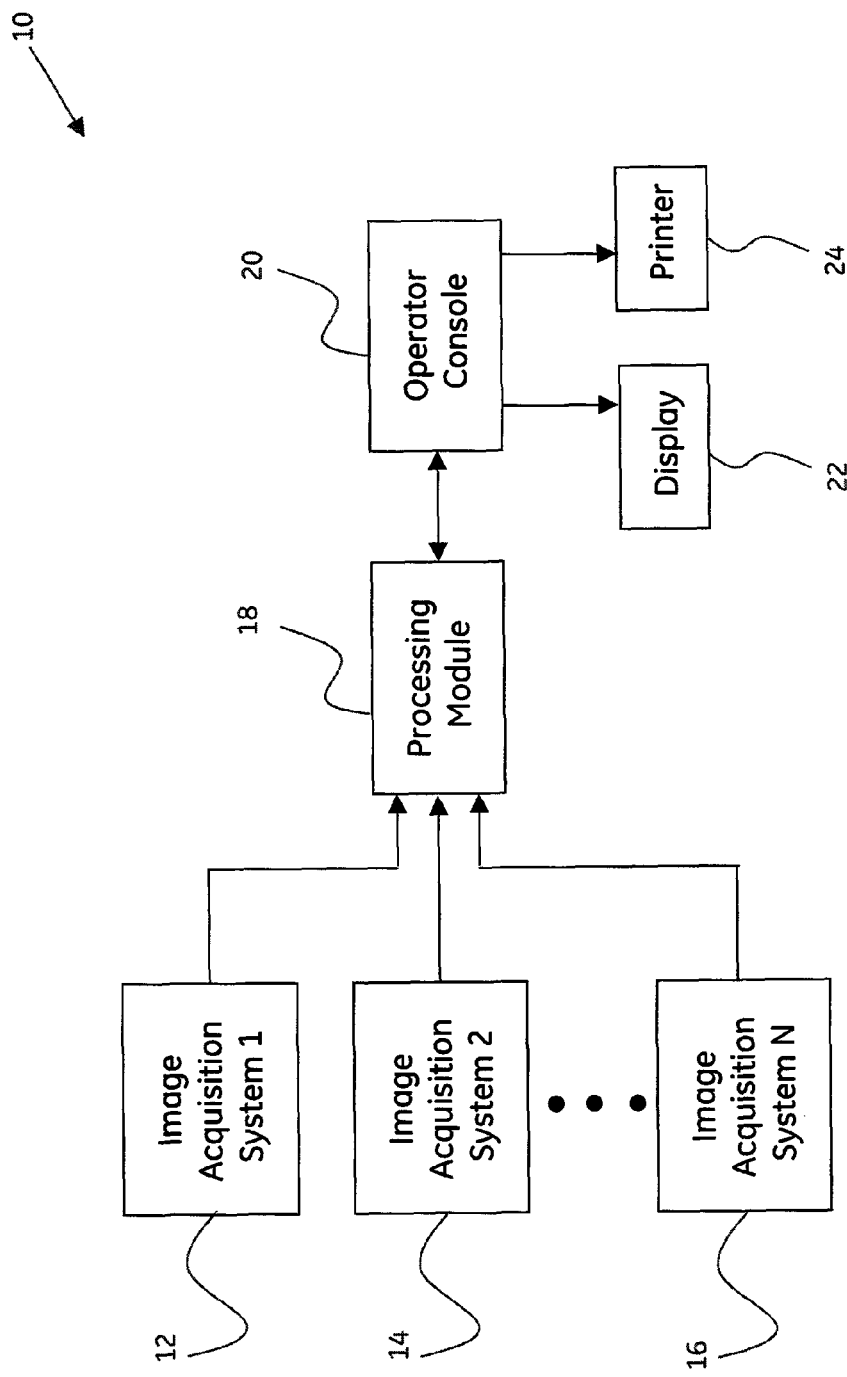
FIG. 1 is a block diagram of an exemplary diagnostic system, in accordance with aspects of the present technique.

FIG. 1 is a block diagram of an exemplary system 10 for use in imaging, in accordance with aspects of the present technique. More particularly, the system 10 may be configured to facilitate volume based registration of two or more image data sets. As will be appreciated by one skilled in the art, the figures are for illustrative purposes and are not drawn to scale. The system 10 may be configured to facilitate acquisition of image data from a patient (not shown in FIG. 1) via a plurality of image acquisition systems. In the illustrated embodiment of FIG. 1, the imaging system 10 is illustrated as including a first image acquisition system 12, a second image acquisition system 14 and an $N^{th}$ image acquisition system 16. It may be noted that the first image acquisition system 12 may be configured to obtain a first image data set representative of the patient under observation. In a similar fashion, the second image acquisition system 14 may be configured to facilitate acquisition of a second image data set associated with the same patient, while the $N^{th}$ image acquisition system 16 may be configured to facilitate acquisition of an $N^{th}$ image data set from the same patient.

In accordance with one aspect of the present technique, the imaging system 10 may be representative of a multi-modality imaging system. In other words, a variety of image acquisition systems may be employed to obtain image data representative of the same patient. More particularly, in certain embodiments each of the first image acquisition system 12, the second image acquisition system 14 and the $N^{th}$ image acquisition system 16 may include a CT imaging system, a PET imaging system, an ultrasound imaging system, an X-ray imaging system, an MR imaging system, an optical imaging system or combinations thereof. For example, in one embodiment, the first image acquisition system 12 may include a CT imaging system, while the second image acquisition system 14 may include an ultrasound imaging system and the $N^{th}$ image acquisition system 16 may include a PET imaging system.

Further, in certain other embodiments, the imaging system 10 may include one image acquisition system, such as the first image acquisition system 12. In other words, the imaging system 10 may include a single modality imaging system. For example, the imaging system 10 may include only one image acquisition system 12, such as an ultrasound imaging system. In this embodiment, a plurality of images, such as a plurality of scans taken over a period of time, of the same patient may be obtained by the same image acquisition system 12.

The plurality of image data sets representative of the patient that has been obtained either by a single modality imaging system or by different image acquisition modalities may then be merged to obtain a combined display. As will be appreciated by those skilled in the art, imaging modalities such as PET imaging systems and single photon emission computed tomography (SPECT) imaging systems may be employed to obtain functional body images which provide physiological information, while imaging modalities such as CT imaging systems and MR imaging systems may be used to acquire structural images of the body that may serve as anatomic maps of the body. These different imaging techniques are known to provide image data sets with complementary and occasionally conflicting information regarding the body. It may be desirable to reliably coalesce these image data sets to facilitate generation of a composite, overlapping image that may include additional clinical information which may not be apparent in each of the individual image data sets. More particularly, the composite image facilitates clinicians to obtain information regarding shape, size and spatial relationship between anatomical structures and any pathology, if present.

Moreover, the plurality of image data sets obtained via a single imaging modality system may also be combined to generate a composite display. This composite display may facilitate clinicians to conduct follow-up studies in the patient or in a comparison of an image with normal uptake properties to an image with suspected abnormalities.

The plurality of acquired image data sets may be "registered" so that the image information associated with a region may be viewed from each image data set. These images may then be used to generate a composite display. Image registration techniques may be utilized to coalesce the plurality of image data sets obtained by the imaging system 10 via a processing module 18, in one embodiment. More particularly, the processing module 18 may be configured to aid in the volume based registration of two or more image data sets, in accordance with aspects of the present technique, and will be described in greater detail with reference to FIGS. 2-5. In the example illustrated in FIG. 1, the processing module 18 is operatively coupled to the image acquisition systems 12, 14, 16. As previously noted, image registration may be defined as a process of transforming the different image data sets into one common coordinate system. More particularly, the process of image registration involves finding one or more suitable transformations that may be employed to transform the image data sets under study to a common coordinate system. In accordance with aspects of the present technique, the transform may include transforms, such as, but not limited to, rigid transforms, non-rigid transforms, or affine transforms. The rigid transforms may include, for example, translations, rotations or a combination thereof. Also, the non-rigid transforms may include finite element modeling (FEM), B-spline transforms, Daemon's (fluid flow based) methods, diffusion based methods, optic flow based methods, or level-set based methods, for example. It may be noted that when one of the image data sets is being continually updated, such as a real-time ultrasound two-dimensional (2D) or three-dimensional (3D) image data set, a position sensing system and/or image-based analysis may be used to maintain registration.

As described hereinabove, the processing module 18 may be configured to facilitate the volume based registration of the plurality of acquired image data sets to generate registered image data sets. It has been observed that the patient under observation typically experiences conscious or unconscious movement while being scanned. Consequently, there is some unpredictable change that may occur either internally or externally between the image data sets acquired either via the same imaging modality or via a multi-modality imaging system. The internal changes may be attributed to motion of organs such as the lungs or the colon. Also, the external changes experienced by the patient are indicative of the involuntary movements of the external body parts of the patient. For example, during an abdominal scan using an ultrasound imaging system and a CT imaging system, or even a subsequent ultrasound scan of the patient, it has been generally observed that the position of the patient tends to change. As a result of this movement, there is a misalignment between the images. Consequently, the process of registering the ultrasound scan to a pre-acquired image volume, such as the CT image volume, may be a laborious and time-consuming process. There is therefore a need for a volume based image registration process that may be tailored to permit substantially superior registration of two or more image data sets. In one embodiment, the processing module 18 may be configured to facilitate implementation of such a volume based image registration process.

The processing module 18 may be accessed and/or operated via an operator console 20. The operator console 20 may also be employed to facilitate the display of acquired images and/or the composite registered image generated by the processing module 18, such as on a display 22 and/or a printer 24. For example, an operator, such as a clinician, may use the operator console 20 to designate the manner in which the registered image is visualized on the display 22.

Figure 2A:
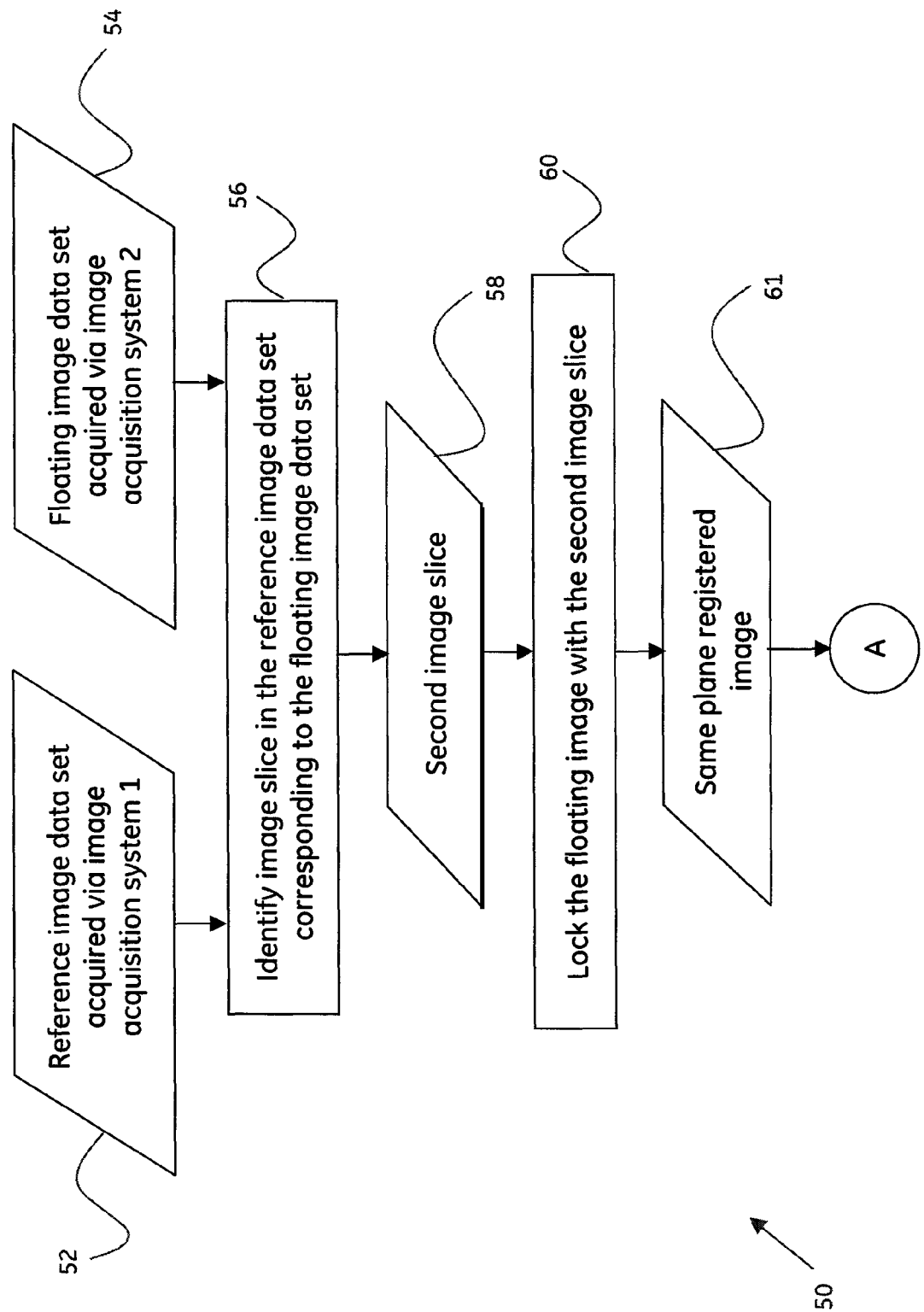
FIGS. 2A-2B are flow charts illustrating an exemplary method of volume based imaging, in accordance with aspects of the present technique.
Figure 2B:
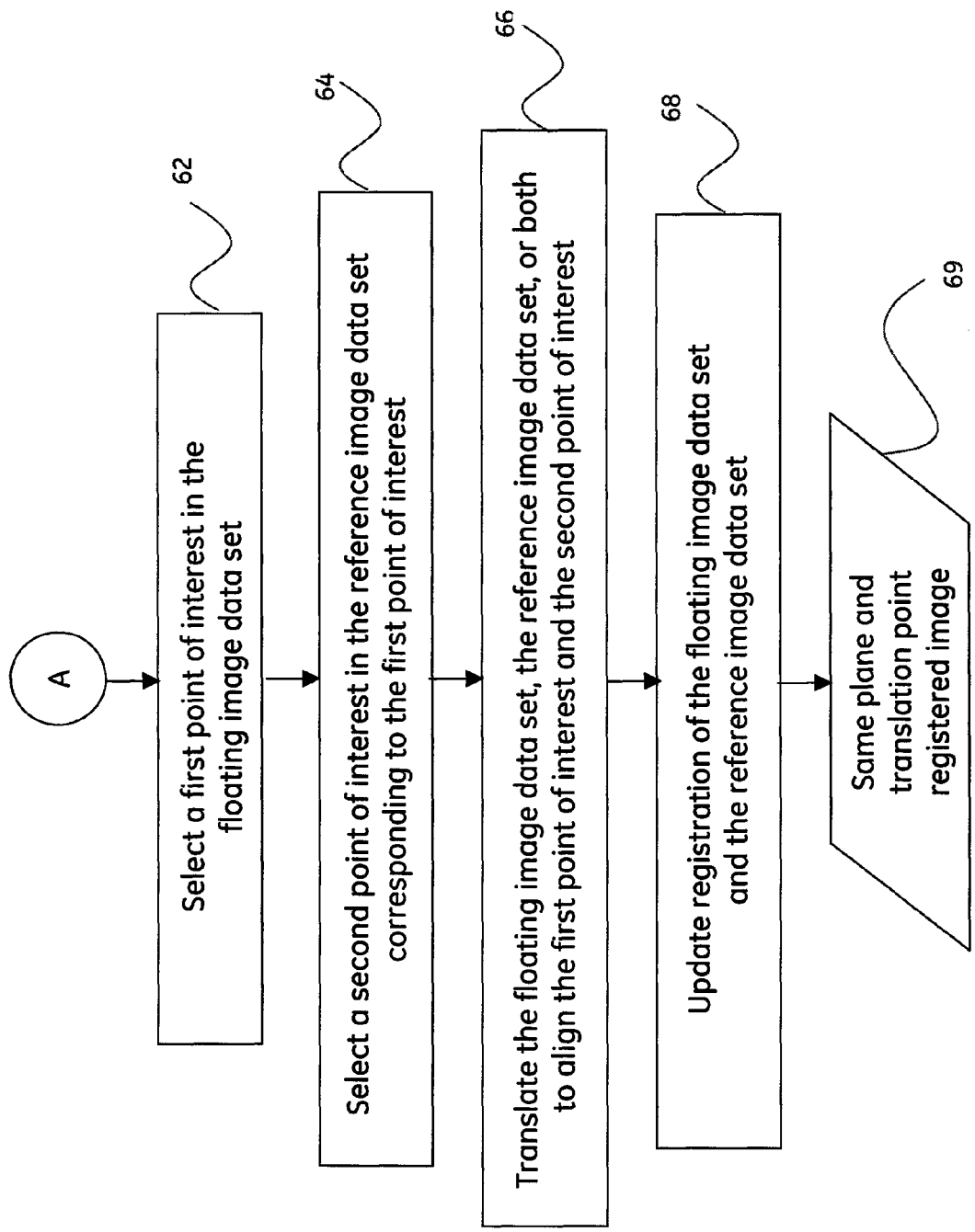

Turning now to FIGS. 2A-2B, a schematic flow chart 50 representative of the operation of the imaging system 10 of FIG. 1, and more particularly of the processing module 18, is depicted. In other words, a method of volume based registration using the system 10 (see FIG. 1) is depicted. In the example depicted in FIG. 2, reference numerals 52 and 54 are representative of a first image data set and a second image data set acquired via one or more image acquisition systems, such as image acquisition systems 12, 14, 16 (see FIG. 1). As previously noted, the image data sets 52, 54 may respectively correspond to image data representative of the same patient acquired via different imaging modalities. Alternatively, if a single imaging modality is employed to acquire image data, then the image data sets 52 and 54 embody image data associated with the same patient acquired via the same kind of imaging modality and taken over a period of time.

In the present example, the first image data set 52 may be acquired via the first image acquisition system 12. Further, the first image acquisition system 12 may include a CT imaging system configured to obtain an image volume representative of an anatomical region of interest in the patient, for example. Accordingly, the first image data set 52 may include CT image data. More particularly, in one embodiment, the CT image volume 52 may include a series of parallel planar images (slices) that are in a standard orientation relative to the body of the patient. For example, an abdominal scan in CT is normally done with the patient laying on his back and the slices are parallel to each other and transverse to the patient. Further, the first image data set 52, acquired via the first image acquisition system 12 may be referred to as a "reference" image, where the reference image is the image that is maintained unchanged and thereby used as a reference. It may be noted that the terms reference image, reference image volume, reference image data set, original image, source image and fixed image may be used interchangeably. The reference image data set 52 may be representative of a pre-acquired image volume. It may be noted that the terms reference image data set, pre-acquired image volume, reference image volume and pre-acquired reference image volume may be used interchangeably.

Additionally, the other acquired images to be mapped onto the reference image may be referred to as "floating" images. In other words, the floating image embodies the image that is geometrically transformed to spatially align with the reference image 52. It may also be noted that the terms floating image, moving image, sensed image and target image may be used interchangeably. Accordingly, the second image data set 54 may be acquired via the second image acquisition system 14, for example. Further, in the present example, the second image acquisition system 14 may include an ultrasound imaging system configured to obtain an image representative of the anatomical region of interest, for example. Accordingly, the second image data set 54 may include ultrasound image data. More particularly, in one embodiment, the ultrasound image data 54 may include a two-dimensional (2D) planar image (slice). Here again, an abdominal scan in ultrasound is normally performed with the patient lying on his back, but given the free movement of the ultrasound probe, there may be no direct correlation to the transverse CT slices. It may be noted that the second image data set 54 may include a 2D ultrasound image that is acquired in real-time. This 2D ultrasound image may also be referred to as a "live" ultrasound image. Alternatively, the second image data set 54 may include multiplanar or 3D ultrasound images that are acquired in real-time. Also, it may be noted that the terms second image data set, ultrasound image, first floating image, and first floating image data set may be used interchangeably.

Subsequent to receiving the pre-acquired reference image data set 52 and the first floating image data set 54, the first floating image data set 54 may be registered with the reference image data set 52. More particularly, in accordance with aspects of the present technique, the first floating image data set 54 may be registered with the reference image data set 52 via use of the processing module 18 (see FIG. 1), as depicted by steps 56-69 and will be described in greater detail hereinafter. In other words, the first floating image data set 54 may be geometrically transformed by the processing module 18 to spatially align with the reference image data set 52, in certain embodiments.

Additionally, in certain embodiments, an optional preprocessing step (not shown in FIG. 2) may be applied to the reference image data set 52 and the first floating image data set 54 prior to being processed by the processing module 18. For example, an image smoothing and/or an image deblurring algorithm may be applied to the reference image data set 52 and the first floating image data set 54 prior to being processed by the processing module 18.

According to exemplary aspects of the present technique, processing by the processing module 18 may be described with reference to steps 56-69. In a presently contemplated configuration, the reference image data set 52 may include an image volume representative of the anatomical region of interest. Moreover, the reference image volume or data set 52 may include a plurality of substantially parallel planar image slices. Further, although, as previously noted, the reference image volume 52 is described as including image data acquired via a CT imaging system, it may be noted that the reference image volume 52 may also include image data acquired via an MR imaging system, a PET imaging system, an X-ray imaging system, a nuclear medicine imaging system, a SPECT imaging system, or an ultrasound imaging system.

Further, in the present example, the first floating image data set 54 may include a first image slice acquired via the second image acquisition system 14 (see FIG. 2). It may be noted that the terms first image slice and floating image may be used interchangeably. In the present example, the first image slice may include a 2D image slice, such as a 2D ultrasound image, representative of the anatomical region of interest, as previously noted. Accordingly, the reference image data set 52 and the first image slice 54 may be configured to serve as inputs to the processing module 18. The processing by the processing module 18 starts at step 56 where an image slice in the reference image data set 52 that corresponds to the first image slice 54 may be identified. This image slice in the reference image data set 52 may generally be referred to as a second image slice 58.

In accordance with aspects of the present technique, the second image slice 58 may be identified via use of the processing module 18 (see FIG. 1), for example. The second image slice 58 in the reference image data set 52 is identified as an image slice that is substantially similar to the first image slice 54. Position sensor and/or image based processing may be used to continually keep the data sets registered as the position of a live ultrasound image, such as the ultrasound image data set 54, is updated.

As will be appreciated, the two planes, namely, the first image slice 54 and the second image slice 58 identified in the pre-acquired reference image data set 52, are representative of a substantially similar image data set. However, image data within the first image slice 54, the second image slice 58, or both may be shifted. In other words, image data in the first image slice 54 and the second image slice 58 may be misaligned. Using the currently available techniques, this misalignment is typically overcome by translating one of the first image slice 54, the second image slice 58 or both in an X-direction, a Y-direction, or both. Unfortunately, there exist inherent challenges in the identification of the second image slice 58 in the reference image volume 52 that is substantially similar to the first image slice 54. In addition, the process of ensuring that the two image slices are substantially parallel to one another is also a challenging task. Further, use of the currently available techniques fails to account for any shifts in a Z-direction.

In accordance with exemplary aspects of the present technique, the shortcomings associated with the currently available techniques may be circumvented by translating one of the first image slice 54, the second image slice 58, or both, in an X-direction, a Y-direction and a Z-direction, thereby facilitating identification of a substantially similar image plane in the reference image data set 52. In one embodiment, an identification methodology, such as, but not limited to, a Plane Lock and Translate Scheme, may be employed to aid in the identification of the second image slice 58 in the reference image data set 52. For example, a user, such as the clinician, may identify a plane in the pre-acquired reference image data set 52 that is substantially similar to the live ultrasound image 54. As will be appreciated, the pre-acquired reference image data set 52 may include a plurality of image slices. Also, each of the plurality of image slices in the reference image data set 52 may be substantially parallel to one another. In one embodiment, the clinician may scan through the pre-acquired reference image data set 52 to identify the substantially similar image plane. It may be noted that the substantially similar image plane may include one the plurality of substantially parallel image slices in the reference image volume 52. Alternatively, the substantially similar image plane may include an image that cuts through the image slices in the reference image volume 52.

Once the substantially similar image plane (second image slice 58) is identified in the pre-acquired reference image data set 52, the clinician may identify a lock thereby tagging the live ultrasound image 54 and the corresponding substantially similar image plane (such as the second image slice 58) in the reference image volume 52 as depicted by step 60. This lock may generally be referred to as a similar plane lock. By way of example, the substantially similar image plane may be identified by scanning through the plurality of CT image slices in the CT reference image volume 52. Also, in a presently contemplated configuration, the clinician may identify the lock by selecting a control on one of the first image acquisition system 12, the second image acquisition system 14, or both. Consequent to the lock at step 60 a same plane registered image 61 may be obtained.

Further, once locked, the two images 54, 58 may be scanned together. In other words, the live ultrasound image 54 may be updated and movement of an image acquisition device, such as a probe including an ultrasound transducer, for example, drives a corresponding new re-sliced image of the pre-acquired volume to be displayed as well. In other words, the ultrasound transducer may include a position sensor operatively coupled to the ultrasound transducer. The clinician may either select a plane from the CT image data 52 or find a substantially similar plane with the ultrasound transducer, or vice versa. In addition, the clinician may indicate the viewing of the similar planes 54, 58 by pressing a key, for example. From that point forward any motions that cause the ultrasound transducer to move may be recorded by the position sensor and may be applied to the CT image data set 52 to pick a new slice, such as the second image slice 68, through the image volume 52. Then, the clinician may identify a point in the CT image data set 52, scan to the same point in the ultrasound image 54 and mark the point. It may be noted that the above process may also be carried out in a reverse order. Once the point is identified in both the image data sets 52, 54, X, Y, and Z shift correction may be performed. As will be appreciated, the two planes, namely, the first image slice 54 and the second image slice 58 identified in the pre-acquired reference image data set 52, are common at this point. Accordingly, consequent to step 56, the second image slice 58 in the reference image volume 52 that is substantially similar to the live image slice 54 may be identified.

However, image data within the first image slice 54, the second image slice 58, or both may be shifted with reference to one another. In other words, image data in the first image slice 54 and the second image slice 58 may be misaligned. Accordingly, image data in the first image slice 54, the second image slice 58, or both may be processed to align the two sets of image data. As noted hereinabove, in accordance with exemplary aspects of the present technique, this misalignment may be addressed by translating one of the first image slice 54, the second image slice 58, or both in the X-direction, the Y-direction, and the Z-direction.

In order to align the first image slice 54 and the second image slice 58, a first point of interest may be selected on the first image slice 54 as depicted by step 62. It may be noted that the first point of interest may include an anatomical structure or a fiduciary marker placed on or in the patient. The first point of interest may be identified using graphical markers, for example. Similarly, at step 64, a second point of interest may be selected in the reference image data set 52. More particularly, the second point of interest may be selected such that the second point of interest is representative of a point that corresponds to the first point of interest in the floating image 54. Also, in one embodiment, the clinician may identify a point in either the ultrasound image 54 or in the pre-acquired reference image data set 52. The point may be selected by placing a cursor over the point in the image and clicking on it, for instance. The clinician may then move the image acquisition device, if necessary, to get the corresponding point of interest in the viewing area on the other image and subsequently select the corresponding point. Although, as described hereinabove, the first point of interest is selected in the floating image 54 followed by the selection of a corresponding second point of interest in the reference image data set 52, it will be understood a first point of interest may be selected in the reference image data set 52 followed by the selection of a corresponding second point of interest in the floating image 54.

Subsequently, at step 66, in accordance with exemplary aspects of the present technique, one of the floating image 54, the reference image data set 52, or both, may be translated in the X-direction, the Y-direction and the Z-direction to facilitate aligning the first point of interest with the second point of interest. Translating the image data sets 52, 54 in the X-direction, the Y-direction and the Z-direction advantageously facilitates compensating for any Z-shift error that was present when the plane lock was established. Consequent to this translation, the floating image 54 is aligned with the reference image data set 52. Subsequently, registration of the floating image 54 with the reference image data set 52 may be updated, at step 68. Following the updating of the registration at step 68, a registered image 69 may be obtained. This registered image 60 may be referred to as a same plane and translation point registered image. The registered image 69 may then be displayed on a display of one of the first image acquisition system 12, the second image acquisition 14, or both, for instance.

As previously noted, there exist inherent challenges in the identification of the second image slice 58 in the reference image data set 52 that corresponds to the floating image 54. Additionally, it may be desirable that the second image slice 58 is in a known orientation relative to the image slices in the reference image data set 52. For example, it may be desirable that the second image slice 58 is substantially parallel to the floating image 54, thereby circumventing rotation along the X-direction and Y-direction. It may also be desirable that the floating image 54 and the second image slice 58 are not rotated relative to one another, thereby circumventing rotation along the Z-direction. Accordingly, another method of volume based registration is presented.

Figure 3A:
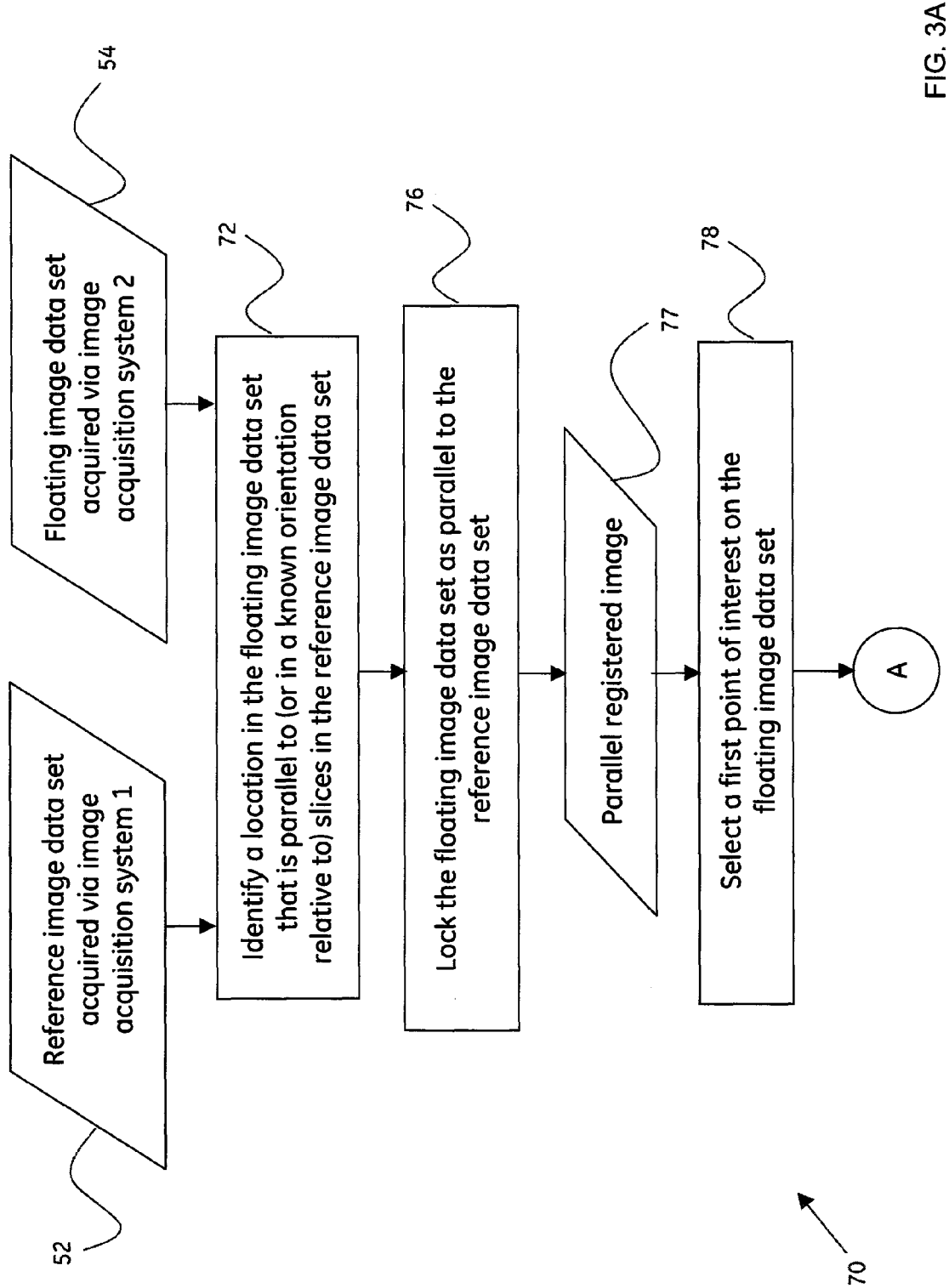
FIGS. 3A-3B are flow charts illustrating another exemplary method of volume based imaging, in accordance with aspects of the present technique.
Figure 3B:
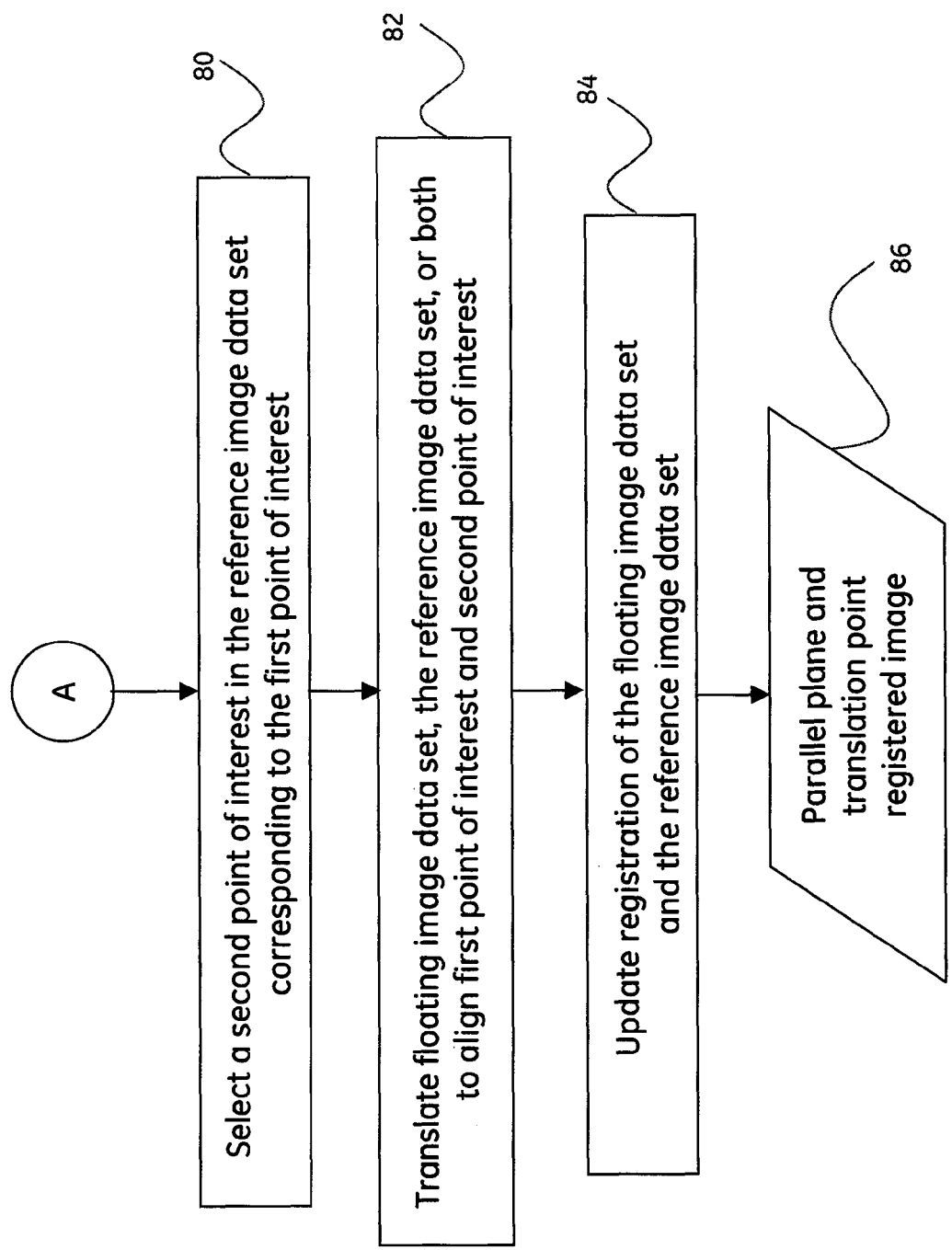

Referring now to FIGS. 3A-3B, a schematic flow chart 70 representative of another method of volume based registration is depicted. In the example depicted in FIG. 3, reference numerals 52 and 54 are representative of the first image data set and the second image data set respectively acquired via one or more image acquisition systems, such as image acquisition systems 12, 14, 16 (see FIG. 1).

Here again, the first image data set 52 may be acquired via the first image acquisition system 12, such as a CT imaging system. Accordingly, the first image data set 52 may include CT image data, where the CT image data may include a series of parallel planar images (slices) that are in a standard orientation relative to the body of the patient. The first image data set 52 may be referred to as a reference image data set 52 and may be representative of a pre-acquired image volume, as previously noted. Also, the second image data set 54 may be acquired via the second image acquisition system 14, such as an ultrasound imaging system configured to obtain an image representative of the anatomical point of interest, for example. The second image data set 54 may include ultrasound image data, where the ultrasound image data 54 may include a 2D planar image (slice). As previously noted, the second image data set 54 may include a 2D ultrasound image that is acquired in real-time. This 2D ultrasound image 54 may also be referred to as a "live" ultrasound image. Alternatively, the second image data set may include multi-planar or 3D ultrasound images that are acquired in real-time.

Subsequent to receiving the pre-acquired reference image data set 52 and floating image 54, the first floating image data set 54 may be registered with the reference image data set 52. In certain embodiments, an optional preprocessing step (not shown) may be applied to the reference image data set 52 and the first floating image data set 54 prior to being processed by the processing module 18 (see FIG. 1). For example, an image smoothing and/or an image deblurring algorithm may be applied to the reference image data set 52 and the first floating image data set 54 prior to being processed by the processing module 18.

The method starts at step 72 where a second image slice in the reference image data set 52 that corresponds to the floating image data set 54 may be identified. More particularly, in accordance with aspects of the present technique, at step 72, a location in the floating image data set 54 that is in a known orientation relative to slices in the reference image data set 52 may be identified. In one embodiment, a location in the floating image data set 54 that is substantially parallel to the slices in the reference image data set 52 may be identified. It may be noted that this location may be located in an image plane in the reference image data set 52, and this image plane be referred to as a "desired" image plane.

As will be appreciated, pre-acquired image volumes, such as those acquired from a CT imaging system or a MR imaging system, for example, typically include a series of parallel planar images (slices) that are in a standard orientation relative to the body of the patient. For example, an abdominal scan in CT is normally conducted with the patient lying on his/her back and the slices are parallel to each other and transverse to the patient. In accordance with exemplary aspects of the present technique, this knowledge of the "acquisition plane" may advantageously be used to enhance the registration scheme. More particularly, in one embodiment, the clinician may scan the floating image data set 54 to identify a location in the floating image data set 54 that is substantially parallel to the slices in the reference image data set 52.

Once the desired location in the floating image volume 54 is identified, the floating image data set 54 may be locked as parallel to the reference image data set 52, as depicted by step 76. This lock may be referred to as a parallel plane lock. Consequent to the locking at step 76, a parallel registered image 77 may be obtained. Subsequently, at step 78, a first point of interest may be identified in the floating image 54. The first point of interest may include an anatomical region of interest, as previously noted with reference to FIG. 2. Further, at step 80, a second point of interest may be identified in the reference image data set 52, where the second point of interest may correspond to the first point of interest. Alternatively, at step 78, a first point of interest may first be selected in the reference image data set 52, while a corresponding second point of interest may be selected in the floating image 54 at step 80.

Further, at step 82, one of the floating image 54, the reference image data set 52, or both, may be translated to align the first point of interest with the second point of interest, as previously described. In other words, one of the floating image 54, the reference image data set 52, or both, may be translated in the X-direction, the Y-direction and the Z-direction to facilitate aligning the first point of interest and the second point of interest. Consequently, the floating image 54 is now aligned with the reference image data set 52. Accordingly, a parallel plane lock between the floating image 54 and the reference image data set 52 may be converted into a same plane lock between the floating image 54 and the reference image data set 52. Moreover, at step 84, a registration of the floating image 54 with the reference image data set 52 may be updated to generate a registered image 86. This registered image 86 may be referred to as a parallel plane and translation point registered image. Subsequently, this registered image 86 may be visualized on a display, such as the display 26 of the system 10 (see FIG. 1).

By implementing the parallel plane lock as described hereinabove, a relatively easier registration of the floating image 54 and the reference image data set 52 may be obtained. Furthermore, as will be appreciated, holding the transducer parallel to the acquisition planes is less prone to error than identifying the same plane in the pre-acquired reference image volume 52, thereby reducing rotational errors.

As described hereinabove, in the present example, a single translation point is employed to convert the parallel plane lock into a same plane lock. However, rotational errors in the X-direction, the Y-direction, and/or the Z-direction, if any, that may have been introduced with the parallel plane lock may not be corrected. In accordance with further aspects of the present technique, the clinician may be allowed to perform a same plane lock using the parallel plane lock as a guide. Accordingly, the clinician may obtain a particular image using the second image acquisition system 14 (see FIG. 1), for example. As previously noted, the second image acquisition image 14 may include an ultrasound imaging system. Hence, an ultrasound image may be obtained. Additionally, the clinician may indicate that this ultrasound image is a desired floating image to lock to. Also, positional information associated with a current position of an image acquisition device may be obtained and stored. The clinician may then scan through image planes in the reference image data set 52 that are parallel to the current ultrasound image slice 54. For example, the clinician may scan through the reference image data set 52 via use of a trackball, mouse, transducer movement or other control mechanisms.

Once the clinician identifies an image plane that is substantially similar to the ultrasound image slice 54, the clinician may indicate a same plane lock. In other words, the clinician may indicate that the ultrasound image slice 54 is to be locked via a same plane lock with this substantially similar image plane in the reference image data set 52. A graphical representation may then be used on the ultrasound image slice 54 to indicate if the ultrasound image slice 54 is substantially parallel to the image plane in the pre-acquired reference image volume 52 based on the parallel plane lock. For example, a point may be displayed in a top right corner of the ultrasound image 54 and/or in a bottom left corner of the ultrasound image 54. It may be noted that it is assumed that the upper left corner of the ultrasound image 54 is in a parallel plane and the two graphics may be used to aid the clinician in adjusting the image acquisition device to be aligned in the same plane as the pre-acquired reference image volume 52. In one embodiment, the graphical markers may include green crosses when that portion of the image is in plane and may be a differently colored square when out of the plane. Further, a direction of being out of plane may be indicated by color, while a desired distance of movement required to get in plane may be indicated by a size of the square and/or an intensity of the color, in certain embodiments. Once the planes are identified as being substantially similar, the clinician may indicate a same plane lock. It may also be noted that the graphical markers may be configured to serve as a guide but are not essential to show parallel in order for the user to specify a same plane lock.

As described hereinabove, the parallel plane technique described hereinabove entails the identification of an image plane that is substantially parallel to the desired image plane or the acquisition plane. Use of the present technique where an image plane of interest may include a plane other than the acquisition plane is also envisaged in accordance with aspects of the present technique. More particularly, it is desirable to know an orientation between the ultrasound transducer in the image acquisition device and the pre-acquired image volume. For example, an ultrasound transvaginal exam may include an ultrasound image that may be rotated by about 90 degrees relative to a standard CT or MR data set. In the present example, the pre-acquired reference image volume may be rotated to a substantially similar orientation as the ultrasound transducer prior to registration. Alternatively, the registration process may include a translation between the ultrasound image and the pre-acquired reference image volume.

In accordance with exemplary aspects of the present technique, information regarding an orientation between the image acquisition device, such as the ultrasound probe, and the pre-acquired image volume may be made available via introduction of a positioning subsystem, where the positioning subsystem may be configured to be in a known orientation relative to a table that the patient is positioned on. In addition, the positioning subsystem may be configured to support the probe in a known orientation relative to the patient table. As will be appreciated, typically, the patient is positioned on a table of a volume scanning device such as a CT scanner. The table may be moved to position the patient for a volume scan. Subsequently, the table may be moved to a new position for an ultrasound scan. By introducing the positioning subsystem that is in a known orientation to the volume scanning device table (CT imaging system, for example) and configured to position the image acquisition device in a known orientation relative to the table, a parallel plane lock may be achieved by simply placing the image acquisition device in the positioning subsystem and indicating to the imaging system 10 (see FIG. 1) that the probe is in this known orientation. Alternatively, a position sensor may be disposed in a known orientation relative to the table and thereby employed to achieve a parallel plane lock without any action by the clinician. Once the registration between the ultrasound image and the pre-acquired image volume is achieved, any table movements from the volume scanning device may be used to update the registration. Alternatively, if the position sensor is attached to the table such that the position sensor moves with the patient, then table movements, if any, do not warrant any adjustments.

The technique described hereinabove may also find application if the patient is moved from the volume scanning device table to a different table or patient holding device. Here again, if the patient is in a substantially similar relative position on the new table as the scanning device table and the probe position or position sensor is in a known orientation relative to the patient, then a parallel plane may be identified. It may be noted that the present example may entail some adjustment of the registration due to probable changes in the patient position. Furthermore, means for manually performing rotational adjustments in the X-direction, the Y-direction and/or the Z-direction to enhance the registration may be provided in accordance with aspects of the present technique.

As previously noted, any Z-shift errors that are present when the plane lock is established may be substantially eliminated by simultaneously performing a shift in the Z-direction in addition to shifts in the X-direction and the Y-direction. It may be noted that if the point of interest used for translation corresponds to an area of interest in the image, any X, Y or Z-axis rotation around the area of interest may be substantially minimized. This step may be repeated to minimize any rotational errors at other points of interest throughout the exam.

Moreover, in accordance with further aspects of the present technique, means for returning to the registration based on a prior point may also be provided. In other words, manual means may be provided to the clinician to correct any rotational error that may occur when the parallel planes are identified. The clinician may be provided with controls to adjust the rotation of the plane about the X, Y and Z-axis. This rotation may be done about a center of the image, a selectable point, or about the last point identified as part of the translation process. The rotational adjustment controls adjust the rotation of the displayed plane in the pre-acquired image volume. The clinician may perform this adjustment while scanning live or on a frozen image. In one embodiment, the manual means for performing the rotation may include rotary controls or a trackball. By way of example, if the manual means includes rotary controls, three rotary controls may be employed to separately adjust rotations about the X-axis, the Y-axis, and the Z-axis.

However, if the manual means includes a single rotary control, then it may be desirable to include a switch configured to switch between the active axes. As will be appreciated, switching between axes entails an extra step for the clinician. In addition, turning a rotary clockwise and/or counterclockwise to achieve a rotation about the X-axis or the Y-axis may not be intuitive because the physical directional movement may not match the physical rotation of the image. For example, an adjustment about the X-axis rolls the image up and away or down while clockwise and counterclockwise movements of the rotary control do not match these motions. Use of a trackball control calls for means to select the axis of rotation and/or means to indicate that the trackball is to be used to perform rotational adjustments as opposed to another user function that may be mapped to the trackball. In accordance with aspects of the present technique, these shortcomings may be circumvented via use of a 4-position (or more than 4-position) joystick rotary. This 4-position joystick rotary may be pushed up or down to affect X-axis rotation, pushed left or right to affect Y-axis rotation and dialed clockwise or counterclockwise to affect Z-axis rotation. Further, holding the key in the up, down, left or right position may optionally cause an accelerated movement. In addition, pushing the control in may be configured to adjust the speed of motion for the adjustments, thereby permitting the clinician to perform gross movements or fine movements.

By implementing the control as described hereinabove, all controls for effecting rotational adjustments are available without selection and the key motions match the image adjustment, making the use much more intuitive. Pushing the control may have a different effect such as changing the control from performing rotational adjustment to doing shift adjustments. In this case left and right motions may perform shifts along the X-axis, up and down motions may perform shifts in the Y-axis, and clockwise and counterclockwise motions may perform Z-shift adjustments.

Additionally, implementing the method of volume based registration as described hereinabove entails three steps. A first step involves the identification of an plane in the pre-acquired image volume that corresponds to the floating image plane and the locking of the image planes, a second step calls for the identification of a point of interest on one of the image planes, while a third step entails the identification of a corresponding point of interest in the other image plane. When the plane lock is initially done, the action to initiate locking (such as clicking on the image with a pointer) may be configured to serve as an initial point in the translation algorithm as well. The clinician may then mark the corresponding point in the other image, thereby completing the lock and translate registration with two actions instead of three.

Furthermore, the clinician locks the two data sets causing both images to update as the transducer is moved. The clinician may then mark a translation point in one of the images. The third step is to mark the corresponding point on the other image. To aid in this third step, the first image may be frozen (no live updating) and the translation point may be configured to remain visible in the frozen image. This acts as a reference while scanning to find the same point in the other image.

Additionally, in the first step, the clinician identifies an image plane in the pre-acquired image volume that is substantially similar to the floating image, such as an ultrasound image. Even though no lock has been established between the ultrasound transducer and the pre-acquired image volume, the ultrasound transducer may be utilized to navigate through the pre-acquired image volume to determine an image plane of interest, thereby facilitating surveying of the pre-acquired image volume. Furthermore, additional points of interest may be marked within the volume for later analysis.

Traditionally, three or more points of interest may be identified in the floating image 54 (see FIG. 2) and corresponding three or more points of interest may subsequently be identified in the reference image volume 52 (see FIG. 2) to aid in the registration of images 52, 54. By identifying three or more common points between the ultrasound image 54 and the pre-acquired reference image volume 52, a transformation may be built and used to extract an image plane from the reference image volume 52 that corresponds to a current probe position. This technique entails identification of a point in the ultrasound image 54, via use of a user control, for example, and subsequent identification of a corresponding point in the pre-acquired image volume 52. The identification process may then be repeated a minimum of two more times for different points. One inherent challenge in the three or more point registration scheme is identifying points that are not substantially close together, as close points tend to generate large errors. Further, shortcomings associated with the currently available techniques have been circumvented by avoiding use of points that are substantially close to one another. In other words, a fixed threshold representative of acceptable distances between the points of interest may be selected to avoid use of two or more points that are disposed at substantially close distances. However, the fixed threshold may not be applicable in certain situations. For example, an anatomical region of interest that includes a relatively large volume area, such as the abdomen, may call for a threshold of about 4 cm, while, it may be challenging to identify three or more points of interest that are at least 4 cm apart in an anatomical region of interest having a relatively small volume area, such as the wrist.

In accordance with exemplary aspects of the present technique, by using parameters associated with the ultrasound image 54, the imaging system 10 (see FIG. 1), and more particularly, the processing module 18 (see FIG. 1) may be configured to infer a size of the anatomical region of interest and automatically set an appropriate threshold. The parameters associated with the ultrasound image 54 may include a depth, the transducer, transducer frequency, a zoom region of interest, to name a few. For example, it may be desirable that the points of interest be at least 20% of the image depth away from each other. Consequently, if the anatomical region of interest includes the abdomen, then scanning at 20 cm depth calls for a threshold separation of about 4 cm. In a similar fashion, if the anatomical region of interest includes the wrist, then scanning at 4 cm depth calls for a threshold separation of about 0.8 cm. Although the present example is described in terms of the image depth, it may be noted that the present technique calls for a threshold that scales automatically with the region of interest being scanned.

Moreover, in accordance with further aspects of the present technique, the system 10 (see FIG. 1) and more particularly, the processing module 18 (see FIG. 1) may be configured to automatically discard a point of interest that is relatively close to another point of interest. The processing module 18 may also be configured to replace the original point of interest or use whichever of the two points provides a better translation. This technique may also be extended to more than two points that are identified to be relatively close to one another.

Furthermore, if more than three points are identified, the system 10 may be configured to provide the clinician a registration based on all the points as well as a registration based on the various subsets of the points. The system 10 may be configured to calculate a numeric quality indicator based on the subset of points and also provide a numeric score to the points based on their distances apart. These two numeric values may then be weighted and combined into an overall quality score. The combination of points achieving the best quality score may be used. In addition, the system 10 may be configured to allow the clinician to select from using all the points, using the best subset of points based on the criteria described hereinabove, or using the best three-point subset based on the criteria described hereinabove.

By implementing the technique as described hereinabove, ease of use of the system 10 may be dramatically enhanced. As will be appreciated, in one embodiment, the clinician typically identifies three or more points of interest in the ultrasound image 54 and the corresponding three or more points of interest in the other image in the reference image volume 52. The live ultrasound image 54 is controlled with the transducer and the pre-acquired image volume 52 is controlled with a mouse, trackball or other input device. The identification of these points of interest may be enhanced in accordance with aspects of the present technique. For example, rather than using a standard input device to navigate through the pre-acquired reference image volume 52, the ultrasound transducer may be used to drive the movement. The point, when identified on an image, may be retained as a graphical marker which in turn serves as a reference while the same point is identified in the other image. The clinician may first perform a same plane lock or a parallel plane lock with optional translation and then use that as a guide for registration using the three or more points of interest. Once the point is identified in one of the images, that image stops updating and the identified point remains visible with a graphical marker. Further, subsequent to the identification of the corresponding point in the second image, the two images return to real-time updating so that the next point may be identified. If a translation point is identified as part of the same plane lock, that point of interest may be used as one of the three or more points of interest. For each pair of points, the clinician may specify which image to identify the first point of interest in. This may vary from one pair of points to the next. Once the first point of a point pair is identified by the clinician, the point of interest may be undone by the clinician. The clinician may also choose to undo a point pair.

As previously noted, there exist several techniques for registering an ultrasound image, such as the floating image 54, with a pre-acquired volume data set, such as the reference image volume 52. For example, the techniques may include a plane lock with an optional translation point, a plane lock with a manual overlay adjustment, a plane lock with an automatic image alignment, a parallel acquisition plane lock with a translation point, and three or more common points in each data set and build a transformation. The overlap and unique aspects of these various registration techniques provide interesting opportunities for efficiency and user flexibility. Performing a manual same plane lock is a common way to initiate registration as the transducer may then be used to adjust both images and therefore aid in the other registration techniques. One advantage is that if a same plane lock with an optional translation point is done, the translation point may be used as the first point in the registration using three or more points of interest.

Accordingly, the clinician may generate multiple translation points. In other words, once a plane lock is identified, the clinician may identify at least three common and independent translation points. The system 10 may be configured to switch to a transformation built from the three or more points to perform the registration of the image slices. The switch may be done automatically or based on user selection. It may be noted that the three or more points may be disposed at a distance greater than a corresponding threshold.

By implementing a plane lock with an optional translation point, the volume based registration of the first image slice 54 and the reference image volume 52 may be dramatically enhanced. More particularly, the speed of registration and the quality of the registration may be enhanced as the entire reference image data set 52 need not be scanned, in accordance with aspects of the present technique.

Moreover, after performing a registration of any type, it may become apparent over time or at a different anatomical location that the image registration is not as good as desired. Accordingly, the clinician may initiate another volume based registration. Furthermore, the system 10 may be configured to keep track of the results for all of the registration methods and allow the clinician to select an appropriate registration. For example, the clinician may perform a plane lock with an optional translation point and subsequently follow up with a three or more point registration. Both registration results may be stored in the system 10, thus allowing the clinician to easily return to the plane lock with optional translation point registration when desired. In addition, the system 10 may also be configured to allow the clinician to save the current registration at any time and allow the corresponding ability to return to that registration when desired. These saved registrations may be multiple registrations of the same technique and/or multiple registrations using multiple techniques. As will be appreciated, each registration method may entail multiple registrations.

In accordance with aspects of the present technique, the last N number of registrations using each method may be saved, thereby providing the clinician an easy way to return to a previous setting. These multiple registration settings may be maintained throughout the course of the patient exam even if the clinician performs other ultrasound imaging techniques that do not require any registration. Furthermore, the various registration techniques may also be combined to minimize the errors. For example, the plane lock with optional translation point may be combined with the three or more point registration. This approach may be used to minimize the errors from the various techniques.

Also, as will be appreciated, when performing a continuous image-based registration, the image information may not be sufficient to maintain tracking. By way of example, if the image acquisition device loses contact with the body or is scanned over a bone or other such objects which ultrasound does not penetrate, the acquired image data may not be sufficient to maintain tracking. Accordingly, the system 10 may be configured to automatically switch to a position sensor based registration. Alternatively, the system 10 may be configured to switch to a position sensor based registration based on user input. Once the images are auto-registered, the system 10 may be configured to automatically switch back to a continuous volume based registration.

The registration techniques described hereinabove are based on anatomical registration. However, non-anatomical aids may also be employed to aid in the registration of the images. Accordingly, when CT or MR data is obtained, a marker may be placed on the body that shows up in the data set. Employing the same marker or via another indicator, the same location may then be marked on the body as well. Further, when performing the ultrasound scan the transducer may be placed on this mark and registered to the part of the data set containing the marker. One marker may be used to aid a plane lock with optional translation point. Multiple markers may be used to aid in a three or more point registration.

As will be appreciated, if a multi-plane or volume transducer is used to facilitate the acquisition of image data, the registration process happens relative to the displayed ultrasound image. It may be noted that different positions of the transducer may be used to facilitate different aspects of the registration. Accordingly, different acquisition planes relative to the transducer may also be used. Once registration has been completed, then as the acquisition plane changes, the relative position of the new acquisition plane may be used to adjust the corresponding slice in the pre-acquired volume. This may be accomplished as the acquisition plane changes in either discrete or continuous steps.

Figure 4A:
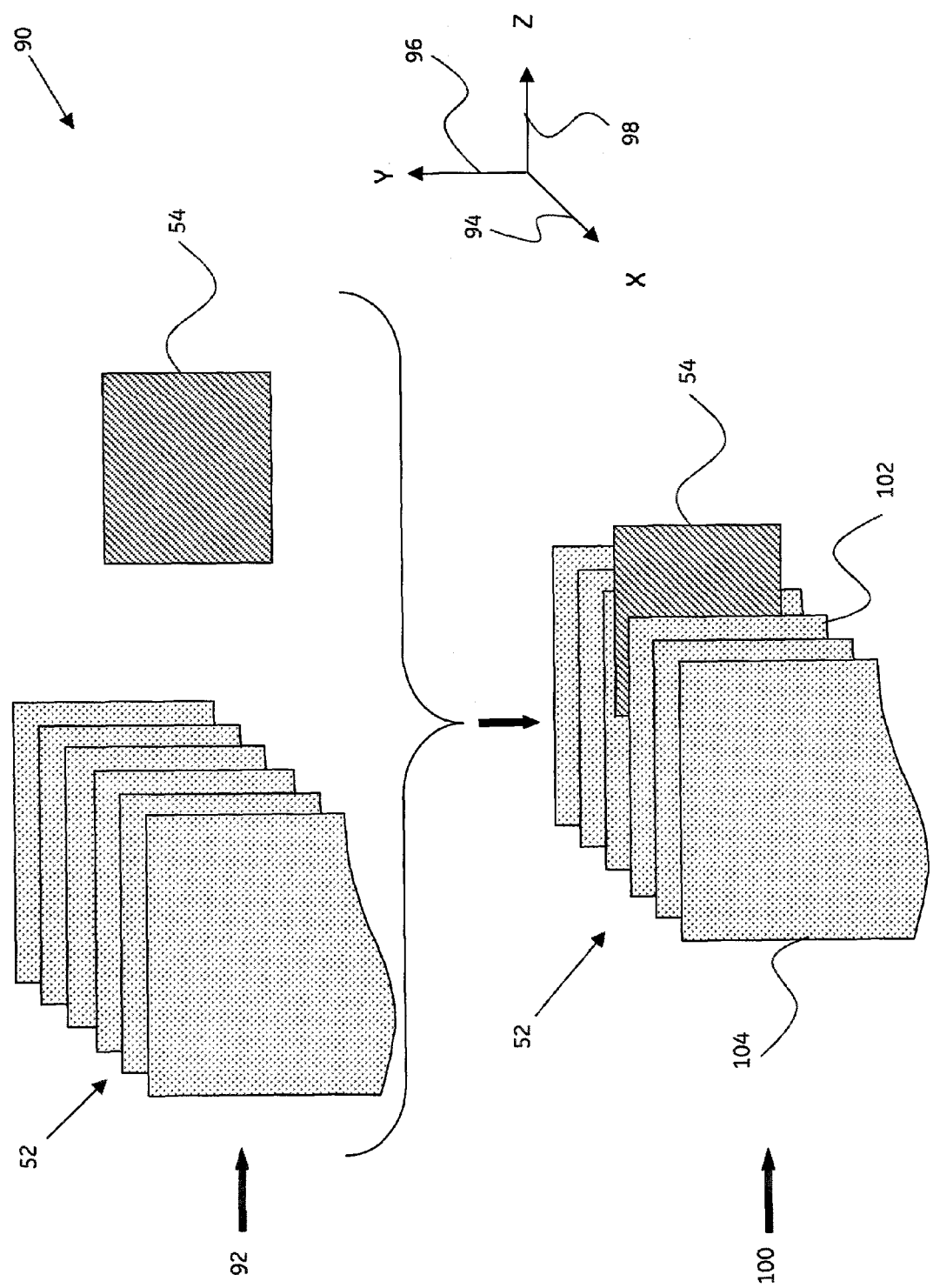
FIGS. 4A-4B are diagrammatic illustrations of an exemplary process of volume based registration, in accordance with aspects of the present technique.
Figure 4B:
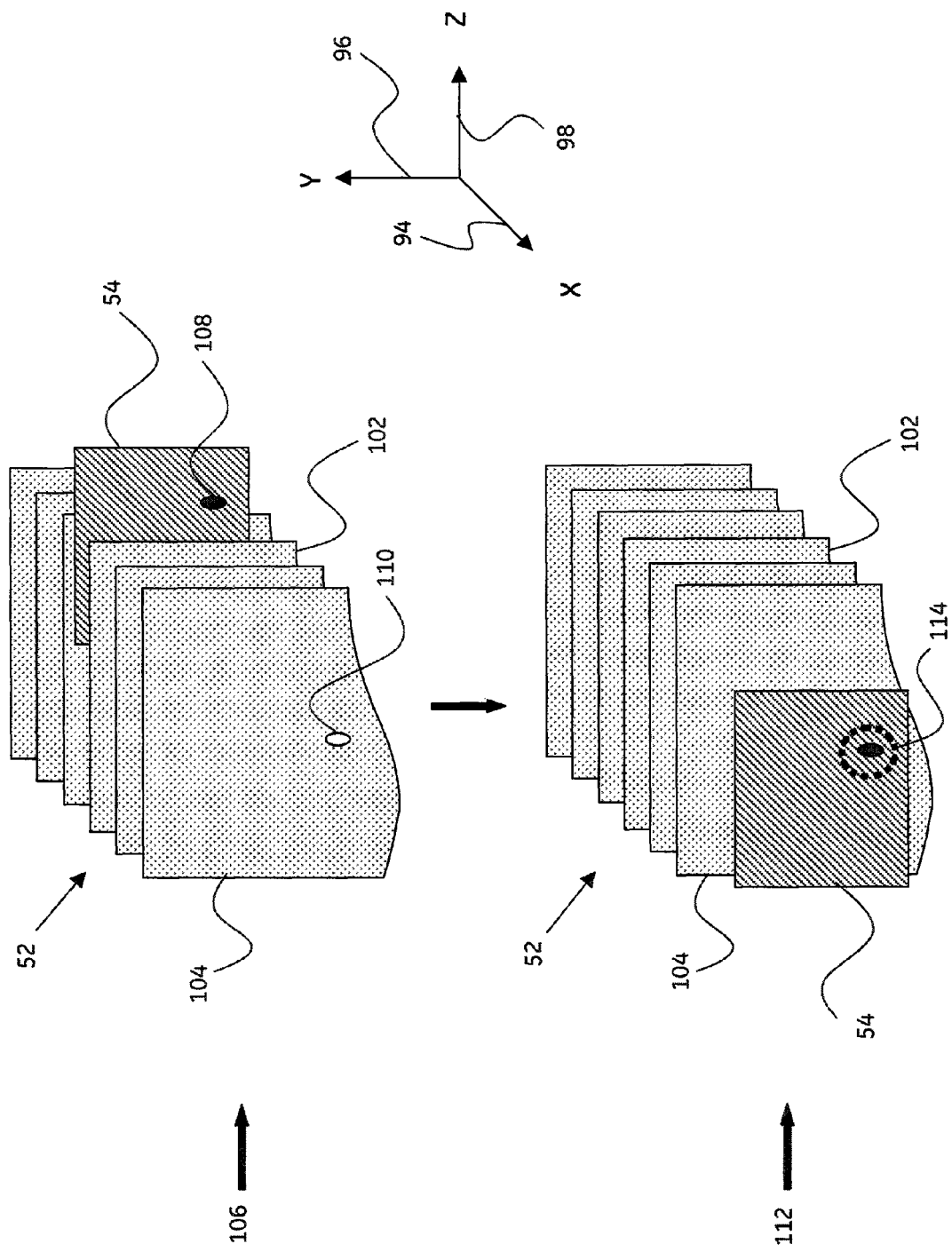

The method of volume based registration of images described hereinabove may be better understood with reference to FIGS. 4A-4B. Referring now to FIGS. 4A-4B, a diagrammatical representation 90 of the method of volume based registration, in accordance with aspects of the present technique, is illustrated. More particularly, FIGS. 4A-4B represent a diagrammatical representation of the method of volume based registration depicted in FIGS. 3A-3B. In the example depicted in FIG. 4, a reference image data set 52 is acquired via a first image acquisition system, such as the first image acquisition system 12 (see FIG. 1), as previously noted. Additionally, at least one other image data set 54 may be acquired via a second image acquisition system, such as the second image acquisition system 14 (see FIG. 1). It may be noted that in one embodiment, each of the reference image data set 52 and the at least one other image data set 54 may be obtained via a plurality of image acquisition systems, as previously described. For example, the first image data set 52 may be acquired via a CT imaging system, while an ultrasound imaging system may be utilized to acquire the at least one other image data set 54. Alternatively, each of the first image data set 52 and the at least one other image data set 54 may be acquired via a single imaging system, such as an ultrasound imaging system. Accordingly, the first image data set 52 and the at least one other image data set 54 acquired via a single imaging system may be representative of scans of the same patient taken at different points in time. Although FIG. 4 depicts a system that uses 2 image data sets, one of ordinary skill in the art will appreciate that the depicted method may be generally applicable to imaging systems employing two or more image data sets.

As previously noted, the first image data set 52 may be referred to as a reference image volume. Similarly, the at least one other image data set 54 may be referred to as a floating image. In addition, an optional preprocessing step (not shown) may be performed on each of the reference image volume 52 and the floating image 54 to enhance quality of the acquired image data sets. In certain embodiments, each of the reference image volume 52 and the floating image 54 may be preprocessed via application of a noise removal algorithm, an image smoothing and/or an image deblurring algorithm.

Each of the reference image volume 52 and the floating image 54 may be processed by the processing module 18 (see FIG. 1). More particularly, the processing module 18 may be configured to facilitate the registration of the reference image data set 52 and the floating image data set 54. The method starts at step 92, where a pre-acquired image volume, such as the reference image data set 52 and a floating image data set, such as the floating image data set 54 are obtained. Also, an X-direction may be represented by reference numeral 94, while reference numeral 96 may be indicative of a Y-direction. In addition, reference numeral 98 may be representative of a Z-direction.

Subsequently, at step 100, in accordance with aspects of the present technique, a location in the floating image data set 54 that is in a known orientation relative to slices in the reference image data set 52 may be identified. It may be noted that in certain embodiments the location may include an image slice in the reference image data set 52 and this location may generally referred to as a desired image plane. In one embodiment, a location in the floating image data set 54 that is substantially parallel to the slices in the reference image data set 52 may be identified, as depicted by step 100. In the present example of FIG. 4, the desired location may include an image slice 102 in the reference image data set 52. Furthermore, with continuing reference to step 100, once the desired location in the floating image volume 54 is identified, the floating image data set 54 may be locked as parallel to the reference image data set 52, as described with reference to FIG. 3. This lock may be referred to as a parallel plane lock, as previously noted. Consequent to the locking at step 100, a parallel registered image may be obtained.

As will be appreciated, image data in the floating image 54 and/or the reference image data set 52 may be misaligned. To address this problem of misalignment of images 52, 54, the image volumes may be aligned based upon a translation in the X-direction 94, the Y-direction 96 and the Z-direction 98 to facilitate enhanced registration. It is therefore desirable to align the floating image 54 and the reference image data set 52. Consequently, in accordance with exemplary aspects of the present technique, one of the floating image 54, the reference image data set 52, or both may be subject a translation in the X-direction 94, the Y-direction 96 and the Z-direction 98 to effect the alignment of the floating image 54 and the reference image data set 52.

Accordingly, at step 106, a first point of interest may be identified in the floating image 54. The first point of interest may include an anatomical region of interest as previously noted. In addition, at step 106, a second point of interest may be identified in the reference image data set 52, where the second point of interest may correspond to the first point of interest. Alternatively, at step 106, a first point of interest may first be selected in the reference image data set 52, while a corresponding second point of interest may be selected in the floating image 54 at step 106.

In the present example, the alignment of the floating image 54 and the reference image data set 52 is depicted in steps 106 and 112. According to aspects of the present technique, at step 106, a first point of interest 108 may be selected in the floating image 54. Furthermore, a second point of interest 110 may also be selected on the reference image data set 52. In the present example, the second point of interest 110 is shown as being selected on an image slice 104. It may be noted that the second point of interest 110 corresponds to the first point of interest 108. Also, the first and second points of interest 108, 110 may be representative of an anatomical structure or a fiduciary marker placed on or in the patient, as previously noted.

Subsequently, at step 112, the floating image 54 may be aligned with the reference image data set 52. Alternatively, the reference image data set 52 may be aligned with the floating image 54. In accordance with aspects of the present technique, the floating image 54 may be aligned with the reference image data set 52 by aligning the first point of interest 108 with the second point of interest 110. More particularly, the floating image 54 may now be moved in the X-direction 94 to align an X-coordinate associated with the first point of interest 108 with an X-coordinate of the second point of interest 110 in the reference image data set 52. Similarly, the floating image 54 may also be moved in the Y-direction 96 with facilitate alignment of a Y-coordinate of the first point of interest 108 with a Y-coordinate of the second point of interest 110. According to exemplary aspects of the present technique, the floating 54 may also be moved in the Z-direction 98 to align a Z-coordinate of the first point of interest 108 in the floating image 54 with a Z-coordinate of the second point of interest 110 in the reference image data set 52. By way of example, position coordinates of the first point of interest 108 may generally be represented by $(X_1, Y_1, Z_1)$, while $(X_2, Y_2, Z_2)$ may be indicative of position coordinates of the second point of interest 110. In the present example, the floating image 54 may be aligned with the reference image data set 52 by translating the floating image 54 in the X-direction 94, the Y-direction 96 and the Z-direction 98. More particularly, the floating image 54 may be moved in the X-direction 94 such that $X_1$ is aligned with $X_2$. Similarly, the floating image 54 may be moved in the Y-direction 96 to facilitate alignment of $Y_1$ with $Y_2$. The floating image 54 may also be moved in the Z-direction 98 such that $Z_1$ is aligned with $Z_2$. Reference numeral 114 may be representative of a region where the first point of interest 108 is aligned with the second point of interest 110. Consequent to step 112, the first point of interest 108 in the floating image 54 may be spatially aligned with the second point of interest 110 in the reference image data set 52, thereby facilitating the alignment of the floating image 54 with the reference image data set 52.

Consequently, the floating image 54 is now aligned with the reference image data set 52. Accordingly, a parallel plane lock between the floating image 54 and the reference image data set 52 may be converted into a same plane lock between the floating image 54 and the reference image data set 52, as previously noted with reference to FIG. 3. Moreover, a registration of the floating image 54 with the reference image data set 52 may be updated to generate a registered image, such as the parallel plane and translation point registered image 86 (see FIG. 3). Subsequently, this registered image may be visualized on a display, such as the display 26 of the system 10 (see FIG. 1).

Figure 5:
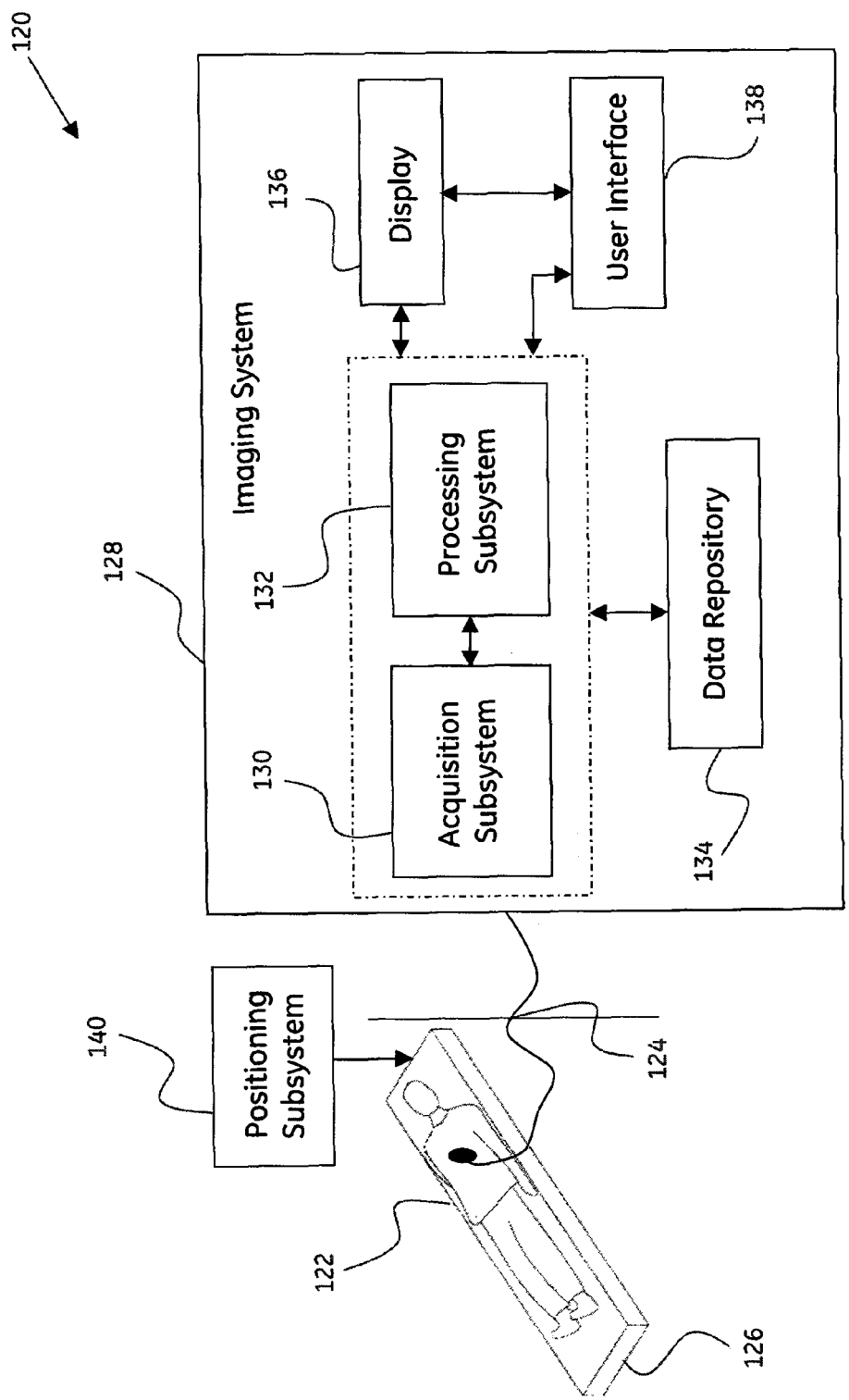
FIG. 5 is a block diagram of a physical implementation of an imaging system configured for use in the exemplary diagnostic system of FIG. 1.

Turning now to FIG. 5, a block diagram 120 illustrating an image acquisition system configured for use in the diagnostic system 10 (see FIG. 1) is depicted. The system 120 may be configured to acquire image data from a patient 122 via an image acquisition device 124. Reference numeral 126 may be representative of a table configured to aid in positioning the patient 122 for an imaging session. In one embodiment, the image acquisition device 124 may include a probe, where the probe may include an invasive probe, or a non-invasive or external probe, such as an external ultrasound probe, that is configured to aid in the acquisition of image data. Also, in certain other embodiments, image data may be acquired via one or more sensors (not shown in FIG. 5) that may be disposed on the patient 122. By way of example, the sensors may include physiological sensors (not shown) such as electrocardiogram (ECG) sensors and/or positional sensors such as electromagnetic field sensors or inertial sensors. These sensors may be operationally coupled to a data acquisition device, such as an imaging system, via leads (not shown in FIG. 5), for example.

The system 120 may also include an image acquisition system 128, such as, but not limited to, a medical imaging system that is in operative association with the image acquisition device 124. In one embodiment, the medical imaging system 128 may include an ultrasound imaging system. It should be noted that although the exemplary embodiments illustrated hereinafter are described in the context of a medical imaging system, other imaging systems and applications such as industrial imaging systems and non-destructive evaluation and inspection systems, such as pipeline inspection systems, liquid reactor inspection systems, are also contemplated. Additionally, the exemplary embodiments illustrated and described hereinafter may find application in multi-modality imaging systems that employ ultrasound imaging in conjunction with other imaging modalities, position-tracking systems or other sensor systems. Furthermore, it should be noted that although the exemplary embodiments illustrated hereinafter are described in the context of a medical imaging system, such as, but not limited to, an ultrasound imaging system, an optical imaging system, a CT imaging system, a MR imaging system, an X-ray imaging system, or a PET imaging system, or a combination thereof, other imaging systems, such as, but not limited to, a pipeline inspection system, a liquid reactor inspection system, a manufacturing inspection system, or other imaging systems are also contemplated in accordance with aspects of the present technique.

In a presently contemplated configuration, the medical imaging system 128 may include an acquisition subsystem 130 and a processing subsystem 132. Further, the acquisition subsystem 130 of the medical imaging system 128 may be configured to acquire image data representative of one or more anatomical regions of interest in the patient 122 via the image acquisition device 124. The image data acquired from the patient 122 may then be processed by the processing subsystem 132.

Additionally, the image data acquired and/or processed by the medical imaging system 128 may be employed to aid a clinician in guiding an interventional procedure, identifying disease states, assessing need for treatment, determining suitable treatment options, and/or monitoring the effect of treatment on the disease states. In certain embodiments, the processing subsystem 132 may be further coupled to a storage system, such as a data repository 134, where the data repository 134 is configured to receive image data.

Further, as illustrated in FIG. 5, the medical imaging system 128 may include a display 136 and a user interface 138. However, in certain embodiments, such as in a touch screen, the display 136 and the user interface 138 may overlap. Also, in some embodiments, the display 136 and the user interface 138 may include a common area. In accordance with aspects of the present technique, the display 136 of the medical imaging system 128 may be configured to display an image generated by the medical imaging system 128 based on the image data acquired via the image acquisition device 124. Additionally, the display 136 may also be configured to display a pre-acquired image volume, such as the reference image data set 52 (see FIG. 2). The display 136 may also be configured to facilitate visualization of a registered image, such as the registered images 69 (see FIG. 2), 86 (see FIG. 3).

In addition, the user interface 138 of the medical imaging system 128 may include a human interface device (not shown) configured to facilitate the clinician in manipulating image data displayed on the display 136. The human interface device may include a mouse-type device, a trackball, a joystick, a stylus, or a touch screen configured to facilitate the clinician to identify the one or more regions of interest. However, as will be appreciated, other human interface devices, such as, but not limited to, a touch screen, may also be employed. Furthermore, in accordance with aspects of the present technique, the user interface 138 may be configured to aid the clinician in navigating through the images acquired by the medical imaging system 128, Additionally, the user interface 138 may also be configured to aid in facilitating the registration of the first image slice 54 (see FIG. 2) with the reference image data set 52, for example.

As previously noted, in certain embodiments, the patient 122 may be positioned on the table of a volume scanning device such as a CT scanner, such as the patient table 126. The table 126 may be disposed in a first position to facilitate setting up the patient 122 for a volume scan and subsequently moved to a second position for an ultrasound scan. In accordance with aspects of the present technique, the imaging system 120 may include a positioning subsystem 140, where the positioning subsystem 140 may be configured to aid in orienting the image acquisition device 124 relative to the table 126. More particularly, the positioning subsystem 140 may be configured to hold the image acquisition device 124 in a known orientation relative to the table 126. In one embodiment, the image acquisition device 124 may be positioned in the positioning subsystem 140, thereby disposing the image acquisition device 124 in a known orientation with respect to the table 126. By placing the image acquisition device 124 in the positioning subsystem 140 as described hereinabove advantageously facilitates obtaining a substantially superior parallel plane lock. In a presently contemplated configuration, the positioning subsystem 140 is shown as being operatively coupled to the table 126. However, as will be appreciated, the positioning subsystem 140 may be disposed at other locations in the system 120. For example, a portion of the positioning subsystem 140, such as a position sensor, that is configured to generate a position sensing field may be attached to the table 126 or otherwise moved with the table 126 such that the position sensing field moves with the patient 122, thereby circumventing any need for adjustments based on table movements.

Alternatively, a position sensor (not shown in FIG. 5) may be employed to aid in orienting the image acquisition device 124 with respect to the table 126. Also, once an image, such as the floating image 54, is registered with a pre-acquired image volume, such as the reference image data set 52, any table movements from the volume scanning device, such as the second image acquisition system 14 (see FIG. 1), may be used to update the registration.

As will be appreciated by those of ordinary skill in the art, the foregoing example, demonstrations, and process steps may be implemented by suitable code on a processor-based system, such as a general-purpose or special-purpose computer. It should also be noted that different implementations of the present technique may perform some or all of the steps described herein in different orders or substantially concurrently, that is, in parallel. Furthermore, the functions may be implemented in a variety of programming languages, including but not limited to C++ or Java. Such code, as will be appreciated by those of ordinary skill in the art, may be stored or adapted for storage on one or more tangible, machine readable media, such as on memory chips, local or remote hard disks, optical disks (that is, CD's or DVD's), or other media, which may be accessed by a processor-based system to execute the stored code. Note that the tangible media may comprise paper or another suitable medium upon which the instructions are printed. For instance, the instructions can be electronically captured via optical scanning of the paper or other medium, then compiled, interpreted or otherwise processed in a suitable manner if necessary, and then stored in a computer memory.

The method for volume based registration of images and the system for volume based registration of images described hereinabove dramatically simplify procedural workflow for the registration of a live ultrasound image with a pre-acquired image volume representative of an anatomical region in the patient and enhance the speed of procedural time taken to accomplish superior registration of the images. Further, use of the method and system advantageously aids in minimizing rotational errors.

The description hereinabove of the embodiments of the methods for volume based registration of images and the system have the technical effect of efficiently registering an ultrasound image with a pre-acquired image volume data set obtained via a single modality or a plurality of imaging modalities, thereby enhancing workflow efficiency while minimizing errors.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for volume based registration of images, the method comprising:
   receiving a first image data set and at least one other image data set;
   identifying a first image slice in the at least one other image data set corresponding to the first image data set;
   selecting a first point of interest in at least one of the first image data set or the first image slice in the at least one other image data set based on a received user input;
   selecting a second point of interest in the other of the first image data set or the first image slice in the at least one other image data set based on a received user input, wherein the second point of interest corresponds to the first point of interest;
   translating one of the first image data set, the first image slice, or both, in at least one of a first direction, a second direction or a third direction to align the first point of interest with the second point of interest; and
   updating registration of the first image data set and the at least one other image data set.

2. The method of claim 1, further comprising locking the first image data set with the first image slice in the at least one other image data set.

3. The method of claim 1, wherein the first image data set is acquired via a first imaging modality and the at least one other image data set is acquired via a second imaging modality, wherein the second imaging modality is different from the first imaging modality.

4. The method of claim 1, wherein the first image data set and the at least one other image data set are acquired via the same imaging modality at different points in time.

5. The method of claim 1, wherein the first image data set is acquired via an ultrasound imaging system.

6. The method of claim 1, wherein the at least one other image data set is acquired via an imaging system, wherein the imaging system comprises one of an ultrasound imaging system, a computed tomography imaging system, a positron emission tomography imaging system, a single photon emission computed tomography imaging system, a magnetic resonance imaging system, an X-ray imaging system, an optical imaging system, or a combination thereof.

7. The method of claim 1, wherein the first direction comprises an X-direction, the second direction a Y-direction, and the third direction a Z-direction.

8. The method of claim 1, further comprising:
identifying a location in the first image data set, wherein the location is in a known orientation to one or more image slices in the at least one other image data set;
selecting a third point of interest in at least one of the first image data set or the at least one other image data set;
selecting a fourth point of interest in the other of the first image data set or the at least one other image data set, wherein the fourth point of interest corresponds to the third point of interest; and
translating one of the first image data set, the at least one other image data set, or both in a first direction, a second direction and a third direction to align the first point of interest with the third point of interest.

9. The method of claim 8, wherein the known orientation comprises a parallel orientation.

10. The method of claim 9, further comprising displaying a graphical marker to indicate whether an image slice is in the parallel orientation.

11. The method of claim 8, further comprising locking the first image data set with the at least one other image data set.

12. The method of claim 8, further comprising recording positional information corresponding to the first image slice.

13. The method of claim 8, further comprising determining a numeric quality indicator based on the selected points of interest, the numeric quality indicator including a numeric score to allow selection of a best sub-set of the selected points of interest.

14. The method of claim 1, further comprising processing the registered image for display.

15. The method of claim 1, wherein the first and second points of interest comprise a fiduciary marker placed on or in a patient.

16. The method of claim 1, wherein the translating comprises transforming the first image data set, the first image slice or both using a non-rigid transform.

17. The method of claim 1, wherein identifying the first image slice in the at least one other image data set results in the registration of the first image data set and the at least one other image data set that is updated.

18. A method for volume based registration of images, the method comprising:
receiving a first image data set and at least one other image data set;
identifying a location in the first image data set, wherein the location is in a known orientation to one or more image slices in the at least one other image data set;
selecting a first point of interest in at least one of the first image data set or the at least one other image data set based on a received user input;
selecting a second point of interest in the other of the first image data set or the at least one other image data set based on a received user input, wherein the second point of interest corresponds to the first point of interest;
translating one of the first image data set, the at least one other image data set, or both, in at least one of a first direction, a second direction or a third direction to align the first point of interest with the second point of interest; and
updating registration of the first image data set and the at least one other image data set.

19. The method of claim 18, further comprising locking the first image data set with the at least one other image data set.

20. The method of claim 18, wherein identifying a location in the first image data set results in the registration of the first image data set and the at least one other image data set that is updated.

21. A non-transitory computer readable medium comprising one or more tangible media, wherein the one or more tangible media comprise:
code adapted to receive a first image data set and at least one other image data set;
code adapted to identify a first image slice in the at least one other image data set corresponding to the first image data set;
code adapted to select a first point of interest in at least one of the first image data set or the first image slice in the at least one other image data set based on a received user input;
code adapted to select a second point of interest in the other of the first image data set or the first image slice in the at least one other image data set based on a received user input, wherein the second point of interest corresponds to the first point of interest;
code adapted to translate one of the first image data set, the first image slice, or both, in at least one of a first direction, a second direction or a third direction to align the first point of interest with the second point of interest; and
code adapted to update registration of the first image data set and the at least one other image data set.

22. The non-transitory computer readable medium, as recited in claim 21, further comprising:
code adapted to identify a location in the first image data set, wherein the location is in a known orientation to one or more image slices in the at least one other image data set;
code adapted to select a third point of interest in at least one of the first image data set or the at least one other image data set;
code adapted to select a fourth point of interest in the other of the first image data set or the at least one other image data set, wherein the fourth point of interest corresponds to the third point of interest; and
code adapted to translate one of the first image data set, the at least one other image data set, or both in a first direction, a second direction and a third direction to align the first point of interest with the third point of interest.

23. The non-transitory computer readable medium, as recited in claim 21, further comprising code adapted to record positional information corresponding to the first image slice.

24. The non-transitory computer readable medium, as recited in claim 21, further comprising code adapted to process the registered image for display.

25. The non-transitory computer readable medium, as recited in claim 21, wherein the code adapted to identify the first image slice in the at least on other image data set results in the registration of the first image data set and the at least one other image data set that is updated.

26. A system, comprising:
- at least one imaging system configured to obtain a first image data set and at least one other image data set; and
- a processing sub-system operationally coupled to the at least one imaging system and configured to process each of the first image data set and the at least one other image data set to generate a registered image based upon a volume based registration of the first image data set and the at least one other image data set based on received user inputs selecting points of interest in the first image data set and the at least one other image data set, wherein the processing sub-system is further configured to:
- receive a first image data set and at least one other image data set;
- identify a first image slice in the at least one other image data set corresponding to the first image data set;
- select a first point of interest in at least one of the first image data set or the first image slice in the at least one other image data set;
- select a second point of interest in the other of the first image data set or the first image slice in the at least one other image data set, wherein the second point of interest corresponds to the first point of interest;
- translate one of the first image data set, the first image slice, or both, in at least one of a first direction, a second direction or a third direction to align the first point of interest with the second point of interest; and
- update registration of the first image data set and the at least one other image data set.

27. The system of claim 26, wherein the first image data set is acquired via a first imaging modality and the at least one other image data set is acquired via a second imaging modality, wherein the second imaging modality is different from the first imaging modality.

28. The system of claim 26, wherein the first image data set and the at least one other image data set are acquired via the same imaging modality at different points in time.

29. The system of claim 28, further comprising a positioning subsystem configured to facilitate orienting an image acquisition device in a known orientation relative to the at least one imaging system.

30. The system of claim 29, further comprising a display configured to display the registered image.

31. The system of claim 26, wherein the processing sub-system configured to identify the first image slice in the at least one other image data set results in the registration of the first image data set and the at least one other image data set that is updated.

* * * * *